United States Patent [19]

Greaney et al.

[11] 4,370,321

[45] Jan. 25, 1983

[54] PROGESTATIONAL ADJUVANT THERAPY

[75] Inventors: Martin O. Greaney; Merritt R. Callantine, both of Evansville, Ind.

[73] Assignee: Mead Johnson and Company, Evansville, Ind.

[21] Appl. No.: 719,558

[22] Filed: Sep. 1, 1976

[51] Int. Cl.³ ............................................. A61K 31/56
[52] U.S. Cl. .................................................... 424/243
[58] Field of Search ........................................ 424/243

[56] References Cited

PUBLICATIONS

Ansfield, et al, Cancer, 33 (1974), pp. 907–909.
Stoll, "British Medical Journal", (1967), No. 3, pp. 338–341.

Primary Examiner—Elbert L. Roberts
Attorney, Agent, or Firm—Robert E. Carnahan

[57] ABSTRACT

Oral treatment with megestrol acetate improves survival rate and reduces the recurrence rate in the adjuvant therapy of breast cancer following mastectomy.

9 Claims, No Drawings

PROGESTATIONAL ADJUVANT THERAPY

FIELD OF THE INVENTION

The present invention involves a drug bioaffecting and body treating process employing a cyclopentanohydrophenanthrene compound which is a prophylactic adjunct following surgery in the management of breast cancer.

DESCRIPTION OF THE PRIOR ART

The 17α-acyloxy-6-methylpregna-4,6-diene-3,20-diones with which the present invention is concerned are the subject of U.S. Pat. No. 3,356,573 patented Dec. 5, 1967. The compounds are progestational agents. The preferred member of the series as disclosed in the patent and for the purposes of the present invention is 17α-acetoxy-6-methylpregna-4,6-diene-3,20-dione which is also known by the non-proprietary name of megestrol acetate. The latter has come into use in clinical medicine for the treatment of endometrial carcinoma and recurrent and metastatic carcinoma of the breast. Other utilities for these substances disclosed in the patent and other literature include the treatment of dysmenorrhea, amenorrhea, endometriosis, oral contraceptive, benign prostatic hypertrophy, and in the treatment of certain other forms of cancer such as prostatic carcinoma and ovarian carcinoma.

With respect to the treatment of recurrent and metastatic cancer of the breast with megestrol acetate, the following publications are pertinent and representative.

Stoll, British Medical Journal, 1967, 3, 338–341.
Ansfield, et al., Cancer, 33, 907–909 (1974).
Brennan, American Journal of Clinical Pathology, 64, 797 (December 1975).
Ansfield, Journal of the American Medical Association, 235, 67–68 (January, 1976).

Stoll describes an exploratory evaluation of various progestational agents in the therapy of breast cancer. Various steroid compounds were tested including megestrol acetate at a daily dose of 30 mg. The patient population consisted of women with advanced breast cancer. That is, the subjects under treatment had existing tumors and one end point evaluated was regression in tumor size.

Ansfield, et al. (1974) describes results in 30 patients with progressing disseminated breast cancer with megestrol acetate at a dose of 160 mg. daily. Again, the patient population bore existing tumors.

The Brennan article involves a theoretical discussion of the role of estrogen receptor cells in the propagation or treatment of cancer of the breast. On page 804 the speculation is offerred that antiestrogens such as megestrol acetate might be useful in medical regimens adjuvant to cancer surgery in patients with estrogen receptorpositive tumors. No experimental work was presented in the article.

Ansfield (1976) discusses the role of adjuvant radiotherapy for breast cancer and announces a five-drug combination consisting of fluorouracil, methotrexate, vincristine sulfate, megestrol acetate, and warfarin sodium as an adjuvant to mastectomy.

SUMMARY OF THE INVENTION

The term adjuvant therapy or adjuvant method of treatment employed with respect to breast cancer refers to prophylactic treatment subsequent to surgical ablation of the tumor with or without radiation. The subject under treatment is diagnostically free of the disease, but is at risk of recurrence possibly due to metastases from the original tumor. In other words, no tumors are detectable by palpation, X-ray, or other currently known means of detection. The present process refers to the adjuvant method of treatment of breast cancer after mastectomy which consists of administering a single drug, namely, a 17α-acyloxy-6-methylpregna-4,6-diene-3,20-dione having up to 10 carbon atoms in the acyloxy group. The preferred compound is 17α-acetoxy-6-methylpregna-4,6-diene-3,20-dione which is known as megestrol acetate. This substance has been previously used in the treatment of recurrent metastatic breast cancer and in the treatment of a number of other forms of cancer, but it has not been previously used as the sole agent in a prophylactic or adjuvant regimen following mastectomy.

DETAILED DESCRIPTION OF THE INVENTION

The following discussion is directed specifically to the adjuvant regimen for the treatment of breast cancer employing megestrol acetate as the sole active ingredient. The regimen with megestrol acetate is intended to be representative of the use of the class of 17α-acyloxy compounds referred to above for this purpose. The invention is applicable to the prophylactic treatment of mammary carcinoma following ablative treatment in all mammalian species which are subject to the disease. The method is primarily of interest, however, in the treatment of human beings and the following discussion is with reference to the treatment of human beings. Other animals of economic value, however, are subject to mammary cancer, for instance, dogs, and the process is applicable to such animals.

Doses in the range of 40–800 mg. per day are employed in practice of the present invention. The daily dose is given preferably in from 2 to 8 divided amounts, and more preferably in 3 to 4 divided amounts. It is preferred to employ oral dosage within the range of 160 mg. to 320 mg. of megestrol acetate per day. Higher doses up to 800 mg. have been administered to humans without toxic effect and doses of that magnitude may be desirable in some circumstances. The lower doses down to about 40 mg. per day may be appropriate in the later stages of treatment when the danger of recurrence is less, for instance, after a period of 5 years following ablation of the tumor. Parenteral forms of treatment, intramuscularly, subcutaneously, or intravenously at equivalent doses may be employed. The preferred route of administration is oral.

Treatment is preferably commenced immediately post-operatively when the patient has recovered from the immediate effects of anesthesia and surgery sufficiently to commence oral medication, and is continued on a daily basis thereafter. The method is applicable, however, at any time following mastectomy when the patient is free of detectable disease and is employed as a prophylactic or preventative measure adjunctively to the surgical and/or radiological ablation of the tumor. A regimen involving dosing each day is preferred, but other repetitive regimens may be followed during the treatment period.

Additional supportive treatment may be employed conjointly with megestrol acetate for the adjuvant therapy of breast cancer according to the present invention. These include digitalis, insulin, nonsteroidal anti-inflammatory agents, and analgesics for the treatment of other co-existing conditions or to make the patient more comfortable. Other active agents customarily used in adjuvant therapy such as cytotoxic agents, anti-metabolites, and hormones are excluded from the regimen. Specifically, combinations of drugs such as those including fluorouracil, methotrexate, vincristine sulfate, warfarin sodium, phenylalanine mustard, adriamycin, etc. are excluded.

The advantages of the present invention are relatively greater effectiveness as compared with proper adjuvant therapy regimens, and lack of toxicity. In the latter regard, most notably absent are the debilitating effects of the cytotoxic agents and the endocrine effects of prior hormonal regimens employing androgens or estrogens. In addition, a sense of well being seems to develop in the subject with an increase in appetite and concomitant weight gain which can be controlled by restricting the caloric intake.

The preferred period of treatment is for the period ending 2-5 years following mastectomy but longer periods may be desirable in the absence of any reason or outside agency, not directly related to the administration of megestrol acetate, ruling in favor of termination of the treatment.

DESCRIPTION OF SPECIFIC EMBODIMENTS

A group of 44 female patients with tumors of one or both breast were selected for adjuvant therapy according to the present invention following mastectomy. The criteria for inclusion in the study were confirmation of the presence of carcinoma and the exclusion of patients where evidence of metastases outside of the curable area of breast and axilla was found. Patients were included having positive axillary lymph nodes. Prior to surgery, a full physical examination was completed and a bone survey was carried out to determine evidence of metastases. A careful record was kept regarding (1) size of the primary lesion, (2) microscopic diagnosis, and (3) number and location of axillary metastases. Following surgery, the patients were placed on a regimen of 160 mg. daily of megestrol acetate administered orally in four equally divided doses with meals and at bedtime. No cytotoxic agents or other hormonal therapy for mammary cancer was employed unless recurrent or metastatic disease appeared. Other treatments such as digitalis, insulin, or analgesics were permitted. Patients were seen every month for the first three months of treatment and thereafter every two months during the first year. After one year, patient visits followed every three months. Procedures applied during the initial examination of the patient and entry into the study including laboratory tests were repeated at six-month intervals or more frequently if it seemed desirable. Evaluation of the treatment was on the basis of (1) survival rate, and (2) length of time from primary therapy until evidence of recurrent disease. Of the 44 patients, five recurrences occurred but four of these had been very serious cases which had at least eight axillary lymph nodes involved at the time of the original mastectomy. Twenty-seven patients were free of the disease after one year, and four of these who had been followed for two years remained free of the disease. The remaining patients were free of the disease, but had been under treatment for less than one year.

What is claimed is:

1. The adjuvant method of treatment of breast cancer after mastectomy which consists essentially of administering an effective non-toxic metastasis preventing oral or parenteral dose of a 17α-acyloxy-6-methylpregna-4,6-diene-3,20-dione having up to 10 carbon atoms in the acyloxy group to a mastectomized mammal said mammal being diagnostically free of mammary carcinoma on a continuing repetitive regimen during a treatment period after mastectomy when the danger of metastatic transmission or recurrence of said cancer exists wherein at the time of mastectomy said mammal had no metastases outside of the curable area of breast and axilla and had positive axillary lymph nodes.

2. The method of claim 1 wherein megestrol acetate is employed.

3. The method of claim 2 wherein said mammal is a human being.

4. The method of claim 3 wherein said period is 2-5 years.

5. The method of claim 3 wherein a daily dosage regimen is employed.

6. The method of claim 3 wherein a non-toxic dose of at least about 40 mg. per day is employed.

7. The method of claim 5 wherein a non-toxic dose of about 160 mg. to 320 mg. per day is employed.

8. The method of claim 3 wherein said treatment period is commenced at a time subsequent to mastectomy prior to any recurrence of the cancer.

9. The method of claim 3 wherein said treatment period is commenced during the post-operative recovery period following mastectomy.

* * * * *